United States Patent
Kurtz et al.

(10) Patent No.: US 6,482,402 B1
(45) Date of Patent: Nov. 19, 2002

(54) ANTIMICROBIAL COMPOSITIONS AND METHODS

(75) Inventors: Caroline Kurtz, Sudbury, MA (US); Thomas X. Neenan, Cambridge, MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/568,825

(22) Filed: May 11, 2000

Related U.S. Application Data

(60) Provisional application No. 60/133,998, filed on May 13, 1999.

(51) Int. Cl.$^7$ .............................................. A61K 31/74
(52) U.S. Cl. ............................... 424/78.17; 424/78.08; 424/78.07; 424/78.02
(58) Field of Search ................ 424/78.1, 78.08, 424/78.02, 78.06, 78.17, 78.07

(56) References Cited

U.S. PATENT DOCUMENTS

| | | | |
|---|---|---|---|
| 2,980,657 A | 4/1961 | Melamed .................... 260/86.1 |
| 3,224,941 A | 12/1965 | Nash et al. .................... 167/55 |
| 3,567,420 A | 3/1971 | Legator et al. ................. 71/67 |
| 3,655,869 A | 4/1972 | Wharton et al. .............. 424/78 |
| 3,923,973 A | 12/1975 | Green et al. .................. 424/78 |
| 3,929,990 A | 12/1975 | Green et al. .................. 424/78 |
| 3,929,991 A | 12/1975 | Steward et al. ............... 424/78 |
| 3,961,042 A | 6/1976 | Green et al. .................. 424/78 |
| 4,005,193 A | 1/1977 | Green et al. ................. 424/168 |
| 4,025,617 A | 5/1977 | Green et al. .................. 424/78 |
| 4,026,945 A | 5/1977 | Green et al. .......... 260/567.6 P |
| 4,035,480 A | 7/1977 | Green et al. .................. 424/78 |
| 4,113,709 A | 9/1978 | Quinlan ........................ 424/78 |
| 4,166,846 A | 9/1979 | Shigematsu et al. .......... 424/81 |
| 4,206,295 A | 6/1980 | Wagner et al. .............. 525/410 |
| 4,217,429 A | 8/1980 | Wagner et al. .............. 525/411 |
| 4,379,137 A | 4/1983 | Ehlers et al. ................. 424/78 |
| 4,407,791 A | 10/1983 | Stark .......................... 424/80 |
| 4,505,926 A | 3/1985 | Newsome et al. .......... 514/398 |
| 4,532,128 A | 7/1985 | Sheldon et al. ............... 424/78 |
| 4,604,404 A | 8/1986 | Munson, Jr. et al. ....... 514/494 |
| 4,621,120 A | 11/1986 | Hollister .................. 525/327.1 |
| 4,826,924 A | 5/1989 | Kourai et al. ............ 525/331.3 |
| 4,843,130 A | 6/1989 | Kourai et al. ............ 525/331.3 |
| 4,889,887 A | 12/1989 | Fan et al. .................... 524/510 |
| 4,959,432 A | 9/1990 | Fan et al. .................... 526/287 |
| 4,960,590 A | 10/1990 | Hollis et al. .................. 424/78 |
| 5,104,649 A | 4/1992 | Jansson et al. ............. 424/78.31 |
| 5,142,010 A | 8/1992 | Olstein ........................ 526/248 |
| 5,149,524 A | 9/1992 | Sherba et al. ............ 424/78.36 |
| 5,208,016 A | 5/1993 | Ohmae et al. ............ 424/78.27 |
| 5,209,922 A | 5/1993 | Merianos et al. ............. 424/46 |
| 5,242,684 A | 9/1993 | Merianos ................. 424/78.07 |
| 5,250,293 A | 10/1993 | Gleich ...................... 424/78.04 |
| 5,298,242 A | 3/1994 | Vanlerberghe et al. ... 424/78.36 |
| 5,300,287 A | 4/1994 | Park ........................ 424/78.04 |
| 5,348,738 A | 9/1994 | Takatsuka et al. ....... 424/78.37 |
| 5,358,688 A | 10/1994 | Robertson .................... 422/28 |
| 5,498,409 A | 3/1996 | Hirayama et al. ....... 424/78.36 |
| 5,536,494 A | 7/1996 | Park ........................ 424/78.04 |
| 6,007,803 A | 12/1999 | Mandeville, III et al. .. 424/78.1 |
| 6,013,635 A | 1/2000 | Heerze et al. ................ 514/25 |
| 6,034,129 A | 3/2000 | Mandeville, III et al. ... 514/549 |
| 6,039,940 A | * | 3/2000 | Perrault et al. .......... 424/78.08 |

FOREIGN PATENT DOCUMENTS

| | | |
|---|---|---|
| EP | 0 042 075 | 12/1981 |
| EP | 0 554 029 | 8/1993 |
| FR | 2 424 290 | 11/1979 |
| GB | 1 508 215 | 4/1978 |
| GB | 2 090 605 | 12/1980 |
| WO | WO 83/01002 | 3/1983 |
| WO | WO 90/09405 | 8/1990 |
| WO | WO 91/04086 | 8/1991 |
| WO | WO 91/12282 | * 8/1991 |
| WO | WO 95/30425 | 11/1995 |

OTHER PUBLICATIONS

Haynie, S. L., et al., "Antimicrobial Activities of Amphiphilic Peptides Covalently Bonded to a Water–Insoluble Resin", *Antimicrob. Agents Chemotherapy*, 39(2): 301–307 (1995).

Maloy, W. L. and Kari, U. P., "Structure–Activity Studies on Magainins and Other Host Defense Peptides", *Biopolymers (Peptide Science)* 37: 105–122 (1995).

Arrowood, M. J., et al., "Hemolytic Properties of Lytic Peptides Active Against the Sporozoites of *Cryptosporidium parvum*", *J. Protozool.* 38(6): 161S–163S (1991).

Mammen, M., et al., "Effective Inhibitors of Hemagglutination by Influenza Virus Synthesized from Polymers Having Active Ester Groups. Insight into Mechanism of Inhibition," *J. Med. Chem.* (38):4179–4190 (1995).

Zlochevskaya, I.V., et al., "Effect of Polyethyleneimine on Certain Fungi," *Mosk. Univ. Biol. Sci. Bull.* 30(3–4):49–52 (1975).

Zalesov, V.S., et al., "Study of the Toxicity Physiological Effect and Antibacterial Activity of Polyethyleneimine," *Nauchn. Tr. Permsk. Farm. Instit.* (4):31–35 (1971). Abstract.

Tashiro, T., "Removal of *Escherichia coli* from Water by Systems Based on Insoluble Polystyrene–Poly(ethylene Glycol)s, –Polyethylenimines, and –Polyethylenepolyamines Quaternized," *J. Polymer Sci.* (34):1369–1377 (1991).

* cited by examiner

Primary Examiner—Thurman K. Page
Assistant Examiner—Blessing Fubara
(74) Attorney, Agent, or Firm—Hamilton, Brook, Smith & Reynolds, P.C.

(57) ABSTRACT

The present invention relates to antimicrobial compositions including pharmaceutical compositions and treatment regimens for preventing or treating a microbial infection in a mammal, such as a human, by administering to the mammal, a therapeutically effective amount of a polymer and a therapeutically effective amount of an antibacterial agent.

7 Claims, No Drawings

ANTIMICROBIAL COMPOSITIONS AND METHODS

RELATED APPLICATION

This application claims the benefit of U.S. Provisional Application Ser. No.: 60/133,998, filed May 13, 1999, the contents of which are incorporated herein by reference in their entirety.

BACKGROUND OF THE INVENTION

The resistance of pathogens to various antimicrobial agents has increased at an alarming rate in recent years rendering many important therapeutics for the treatment of microbial infections ineffective. There exist multiple mechanisms for resistance that have been well studied. Pathogens may employ one or more modes of resistance rendering them polyresistant. Polyresistant pathogens are found among a variety of microorganisms including rendering some treatable by only a single class of clinically available antimicrobial agents, if at all.

In response to the rapid development of polyresistant pathogens, combinations of active antimicrobial therapeutic agents are being employed to treat disease. The most useful combination therapies appear to be capable of inhibiting or killing microbes via multiple mechanisms thereby circumventing microbial resistance.

Thus there is a need for antimicrobial agents or a combination of agents that together possess potent broad spectrum antimicrobial activity to which the microbe can not easily become resistant, and can be administered at lower concentrations while maintaining or improving therapeutic activity, and have reduced toxicity, and are inexpensive to produce.

SUMMARY OF THE INVENTION

In one aspect, the present invention relates to antimicrobial compositions.

Another aspect of the invention deals with pharmaceutical compositions comprising a broad group of known antibacterial agents in combination with polymers of the invention as defined herein and a pharmaceutically acceptable carrier.

Yet another aspect of the invention is a treatment regimen (also referred to herein as the "treatment regimen" or "method" of the invention) for treating a microbial infection in a mammal, comprising administering to the mammal a therapeutically effective amount of polymer as defined herein in combination with a therapeutically effective amount of an antibacterial agent.

The polymer to be administered can be a homopolymer or a copolymer. In one embodiment, the polymer further includes a monomer comprising a hydrophobic group, such as an aryl group or a normal or branched $C_3$–$C_{18}$-alkyl group.

The polymer to be administered can, optionally, further include a monomer comprising a neutral hydrophilic group, such as a hydroxyl group or an amide group.

The polymer can further have a backbone which is interrupted at one or more points by a nitrogen containing functional group such as a quaternary ammonium group, phosphorus containing functional groups, or sulfur containing functional groups.

Preferred polymers of the invention include amine or ammonium functional groups attached to the polymer backbone via aliphatic spacer groups.

The term "antimicrobial agents" are intended to include antibacterial agents, antifungal agents, antiseptics and the like.

The treatment regimen of the invention represents a new approach to antibacterial therapy to which a polymer can be administered in combination with an antibacterial agent to provide a therapeutically effective treatment of an infection, particularly an infection involving resistant or polyresistant bacteria, and/or to reduce the overall amount of antibacterial agent, or polymer necessary to treat an infection.

Furthermore, the treatment regimen of the invention may reduce the need to develop new antibacterial agents as bacteria and other microbes develop resistance to known antibacterial and antimicrobial agents.

In addition, the polymers employed in the invention are easily prepared using standard techniques of polymer synthesis and inexpensive starting materials. Preferably, the polymers will not be substantially degraded in the digestive tract and, therefore, can be administered orally or topically. Polymer compositions can also be readily varied, to optimize properties such as solubility or water swellability and antimicrobial activity.

DETAILED DESCRIPTION OF THE INVENTION

A description of preferred embodiments of the invention follows.

The present invention relates to antimicrobial compositions including pharmaceutical compositions and treatment regimens for preventing or treating a microbial infection in a mammal, such as a human, by administering to the mammal, a therapeutically effective amount of an cationic polymer and a therapeutically effective amount of an antibacterial agent.

As used herein, a "therapeutically effective amount" is a first amount of a polymer in combination with a second amount of an antimicrobial agent that is sufficient to therapeutically inhibit, partially or totally, a microbial infection, or to reverse development of a microbial infection, or prevent or reduce its further progression.

The term "antimicrobial agent" is intended to include antibacterial agents, antifungal agents, antiseptics and the like. The term "antibacterial agent" includes but is not limited to: naturally occurring antibiotics produced by microorganisms to suppress the growth of other microorganisms, and agents synthesized or modified in the laboratory which have either bacteriocidal or bacteriostatic activity, e.g., β-lactam antibacterial agents including, e.g. carbencillim; ampicillin, cloxacillin, oxacillin and pieracillin, cephalosporins and other cephems including, e.g. cefaclor, cefamandole, cefazolin, cefoperazone, ceftaxime, cefoxitin, ceftazidime, ceftriazone and carbapenems including, e.g., imipenem and meropenem; and glycopeptides, macrolides, quinolones (e.g. nalidixic acid), tetracyclines, aminoglycosides (e.g. Gentamicin and Paromomycin) and further includes antifungal agents. In general if an antibacterial agent is bacteriostatic, it means that the agent essentially arrests or inhibits bacterial cell growth (but does not kill the bacteria); if the agent is bacteriocidal, it means that the agent kills bacterial cells (and may stop growth before killing the bacteria).

The term "polymer" refers to a macromolecule comprising a plurality of repeat units or monomers. The term includes homopolymers, which are formed from a single type of monomer, and copolymers, which are formed of two or more different monomers. A "terpolymer" is a copolymer formed from three different monomers. The term polymer, as used herein, is intended to exclude proteins, peptides, polypeptides and proteinaceous materials.

As used herein, the term "polymer backbone" or "backbone" refers to that portion of the polymer which is a continuous chain, comprising the bonds which are formed between monomers upon polymerization. The composition of the polymer backbone can be described in terms of the identity of the monomers from which it is formed, without regard to the composition of branches, or side chains, off of the polymer backbone. Thus, a poly(acrylamide) polymer is said to have a poly(acrylamide) backbone, without regard to the substituents on the acrylamide nitrogen atom, which are components of the polymer side chains. A poly(acrylamide-co-styrene) copolymer, for example, is said to have a mixed acrylamide/styrene backbone.

The term "polymer side chain" or "side chain" refers to the portion of a monomer which, following polymerization, forms a branch off of the polymer backbone. In a homopolymer all of the polymer side chains are identical. A copolymer can comprise two or more distinct side chains. When a side chain comprises an ionic unit, for example, the ionic unit depends from, or is a substituent of, the polymer backbone, and is referred to as a "pendant ionic unit". The term "spacer group", as used herein, refers to a polyvalent molecular fragment which is a component of a polymer side chain and connects a pendant moiety to the polymer backbone. The term "aliphatic spacer group" refers to a spacer group which does not include an aromatic unit, such as a phenylene unit.

The term "addition polymer", as used herein, is a polymer formed by the addition of monomers without the consequent release of a small molecule. A common type of addition polymer is formed by polymerizing olefinic monomers, wherein monomers are joined by the formation of a carbon-carbon bonds between monomers, without the loss of any atoms which compose the unreacted monomers.

The term "monomer", as used herein, refers to both (a) a single molecule comprising one or more polymerizable functional groups prior to or following polymerization, and (b) a repeat unit of a polymer. An unpolymerized monomer capable of addition polymerization, can, for example, comprise an olefinic bond which is lost upon polymerization.

For the treatment regimen of the invention, the appropriate combination of polymer and antibiotic to be administered for treatment of a microbial infection in a mammal will be determined on an individual basis and will be determined, at least in part, by consideration of the individual's size, the severity of symptoms to be treated and the result sought.

The treatment regimen encompasses co-administration of therapeutically effective amounts of polymer and antibacterial agent in a single, substantially simultaneous manner, such as in a single capsule, tablet, injection or topical ointment having a fixed ratio of polymer and antibacterial agent, or in multiple, separate capsules, tablets, ointments or injections for each of the polymer and antibacterial agent. In addition, the treatment regimen also encompasses use of each compound separately, in a sequential manner (e.g. minutes or hours apart).

Each component of the treatment regimen may be administered, for example, topically, orally, intranasally, or rectally. The form in which the agent is administered, for example, powder, tablet, capsule, solution, or emulsion, depends in part on the route by which it is administered. The therapeutically effective amount of each component of the regimen can be administered in a series of doses separated by appropriate time intervals, such as hours.

Microbial infections which can be treated or prevented by the treatment regimen of the invention include bacterial protozoal, viral, ameobic, fungal and parasitic infections, such as infection by Streptococcus, including *Streptococcus mutans, Streptococcus salivarius,* and *Streptococcus sanguis,* Salmonella, Campylobacter, including *Campylobacter sputum* and *Campylobacter jejuni,* Heliobacter, including *Heliobacter pylori,* Antinomyces, including *Actinomyces naeslundii* and *Actinomyces viscosus, Escherichia coli, Clostridium difficile,* Staphylococcus, including *S. aureus,* Shigella, Pseudomonas, including *P. aeruginosa, Eikenella corrodens, Actinobacillus actinomycetemcomitans, Bacteroides gingivalis,* Capnocytophaga, including *Capnocytophaga gingivalis, Wolinell recta, Bacteriodes intermedius,* Mycoplasma, including *Mycoplasma salivarium,* Treponema, including *Treponema denticola, Peptostreptococcus micros, Bacteriodes forsythus,* Fusobacteria, including *Fusobacterium nucleatum, Selenomonas sputigena, Bacteriodes fragilis, Enterobacter cloacae,* Pneumocystis, *Cryptosporidium parvum* and *Giardia lamblia, Entameoba histolytica* or Acanthameoba, such as *A. castellani, Candida albicans, Aspergillus fumigatus,* and *Trichinella spiralis.* The method is useful for treating infections of various organs of the body, but is particularly useful for infections of the skin and gastrointestinal tract.

Suitable polymers for the present treatment method include polymers having amine or ammonium functional groups attached to the polymer backbone via aliphatic spacer groups.

Polymers which are particularly suitable for the present method include polymers that form amphipathic structures. The term "amphipathic", as used herein, describes a three-dimensional structure having discrete hydrophobic and hydrophilic regions. Thus, one portion of the structure interacts favorably with aqueous and other polar media while another portion of the structure interacts favorably with non-polar media. An amphipathic polymer results from the presence of both hydrophilic and hydrophobic structural elements along the polymer backbone.

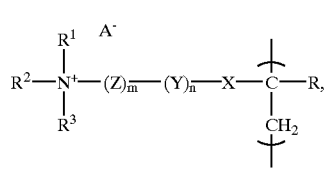

(I)

wherein X is a covalent bond, a carbonyl group or a $CH_2$ group, Y is an oxygen atom, an NH group or a $CH_2$ group, Z is a spacer group, R is a hydrogen atom or a methyl or ethyl group; $R^1$, $R^2$ and $R^3$ are each, independently, a hydrogen atom, a normal or branched, substituted or unsubstituted $C_1$–$C_{24}$-alkyl group, an aryl group or an arylalkyl group; $A^-$ is a pharmaceutically acceptable anion, such as a conjugate base of a pharmaceutically acceptable acid; and m and n are each, independently, 0 or 1. Suitable alkyl substituents include halogen atoms, such as fluorine or chlorine atoms. A monomer of Formula 1 in which at least one of substituents $R^1$, $R^2$ and $R^3$ is hydrogen can also exist in the free base, or amino, form in which a hydrogen substituent is absent and the nitrogen atom is electrically neutral.

In a preferred embodiment, one of $R^1$–$R^3$ is an ammonioalkyl group of the general formula

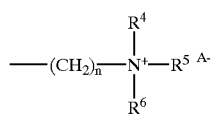

(II)

wherein $R^4$, $R^5$ and $R^6$ are each, independently, a hydrogen atom, a $C_1$–$C_{24}$ alkyl group, or an arylalkyl group; n is an integer from 2 to about 20, preferably from 3 to about 6; and $A^-$ is a pharmaceutically acceptable anion. An ammonioalkyl group in which at least one of substituents $R^4$, $R^5$ and $R^6$ is hydrogen can also exist in the free base, or amino, form in which a hydrogen substituent is absent and the nitrogen atom is electrically neutral. The group $—N^+(R^4)(R^5)(R^6)$ can also be a heteroaryl group, such as a 5- or 6-membered heteroaryl group, such as a 1-pyridinio group. Preferably, at least one of $R^4$, $R^5$ and $R^6$ is a $C_6$–$C_{24}$-alkyl group. Examples of suitable ammonioalkyl groups include, but are not limited to, 4-(dioctylmethylammonio)butyl; 3-(dodecyldimethylammonio)propyl; 3-(octyldimethylammonio)propyl; 3-(decyldimethylammonio)propyl; 5-(dodecyldimethylammonio)pentyl; 3-(cyclohexyldimethylammonio)propyl; 3-(decyldimethylammonio)-2-hydroxypropyl; 3-(tridecylammonio)propyl; 3-(docosyldimethylammonio)propyl; 4-(dodecyldimethylammonio)butyl; 3-(octadecyldimethylammonio)propyl; 3-(hexyldimethylammonio)propyl; 3-(methyldioctylammonio)propyl; 3-(didecylmethylammonio)propyl; 3-(heptyldimethylammonio)propyl; 3-(dimethylnonylammonio)propyl; 6-(dimethylundecylammonio)hexyl; 4-(heptyldimethylammonio)butyl; 3-(dimethylundecylammonio)propyl; 3-(tetradecyldimethylammonio)propyl; 3-(1-pyridinium)propyl; in combination with a pharmaceutically acceptable anion.

When at least one of $R^1$ to $R^6$ is a hydrogen atom, the monomer can also exist in the free base, or amino form. The polymer comprising such a monomer can be administered in the free base form or in the protonated or partially protonated form, for example, as a salt of a pharmaceutically acceptable acid. Suitable acids include hydrochloric acid, hydrobromic acid, citric acid, lactic acid, tartaric acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucoronic acid, oxalic acid, ascorbic acid, and acetylglycine. In either case, at physiological pH following administration, a plurality of amino groups will be protonated to become ammonium groups, and the polymer will carry an overall positive charge.

The spacer group Z is a component of the polymer side chain and connects the amino or ammonium group to the polymer backbone. The amino or ammonium group is, thus, a pendant group. The spacer group can be a normal or branched, saturated or unsaturated, substituted or unsubstituted alkylene group, such as a polymethylene group $—(CH_2)_n—$, wherein n is an integer from about 2 to about 24. Suitable examples include the propylene, hexylene and octylene groups. The alkylene group can also, optionally, be interrupted at one or more points by a heteroatom, such as an oxygen, nitrogen (e.g, NH) or sulfur atom. Examples include the oxaalkylene groups $—(CH_2)_2O[(CH_2)_2O]_n(CH_2)_2—$, wherein n is an integer ranging from 0 to about 3.

Examples of monomers of Formula I having quaternary ammonium groups include:
N-(3-dimethylaminopropyl)acrylamide,
N-(3-trimethylammoniopropyl)acrylamide,
2-trimethylammonioethyl methacrylate,
2-trimethylammonioethyl acrylate,
N-(3-trimethylammoniopropyl)methacrylamide,
N-(6-trimethylammoniohexyl)acrylamide,
N-(3-trimethylammoniopropyl)acrylamide,
N-(4-trimethylammoniobutyl)allylamine,
N-(3-dimethyloctylammoniopropyl)allylamine,
N-(3-trimethylammoniopropyl)allylamine,
N-(3-(1-pyridinio)propyl)vinylamine and
N-(3-(1-pyridinio)propyl)allylamine.

Each of these monomers also includes a suitable counter anion. Examples of monomers of Formula I having an amino group include allylamine, vinylamine and N-(3-dimethylaminopropyl)acrylamide. Each of these monomers can also exist as a salt with a pharmaceutically acceptable acid.

In another embodiment, the polymer to be administered is characterized by a diallylamine repeat unit of Formula III:

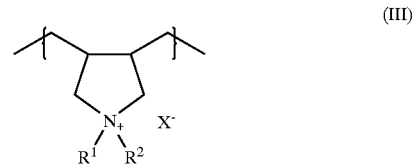

(III)

wherein $R^1$ and $R^2$ are each, independently, a hydrogen atom, a normal or branched, substituted or unsubstituted $C_1$–$C_{24}$-alkyl group, an aryl group or an arylalkyl group; and $A^-$ is a pharmaceutically acceptable anion, such as a conjugate base of a pharmaceutically acceptable acid. Suitable alkyl substituents include halogen atoms, such as fluorine or chlorine atoms. A monomer of Formula III in which at least one of substituents $R^1$ and $R^2$ is hydrogen can also exist in the free base, or amino, form, in which a hydrogen substituent is absent and the nitrogen atom is electrically neutral. In a preferred embodiment, $R^1$ is an ammonioalkyl group of Formula II, as described above.

In another embodiment, the polymer to be administered is a poly(alkyleneimine) polymer comprising a monomer, or repeat unit, of Formula IV,

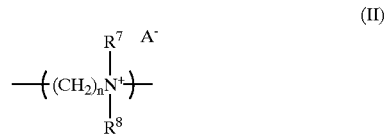

(II)

wherein n is an integer from about 2 to about 10 and $R^7$ and $R^8$ are each, independently, a hydrogen atom, a normal or branched, substituted or unsubstituted $C_1$–$C_{24}$-alkyl group, an aryl group or an arylalkyl group, and $A^-$ is a pharmaceutically acceptable anion. Suitable alkyl substituents include halogen atoms, such as fluorine or chlorine atoms. When one of $R^7$ and $R^8$ is a hydrogen atom, the polymer can be administered in the free base form or in the cationic form shown, as the salt of a pharmaceutically acceptable acid. A monomer of Formula IV in which at least one of substituents $R^7$ and $R^8$ is hydrogen can also exist in the free base, or amino form, in which a hydrogen substituent is absent and the nitrogen atom is electrically neutral. In a preferred embodiment, the polymer to be administered is a poly (ethyleneimine) polymer, comprising a monomer of Formula IV wherein n is 2.

Preferably, $R^7$ is an aminoalkyl group, or an ammonioalkyl group of Formula II, as described above. In one embodiment, the polymer comprises monomeric units of Formula 11 wherein $R^7$ is an aminoalkyl group, or an ammonioalkyl group, as well as monomeric units wherein $R^7$ and $R^8$ are each hydrogen or $R^7$ is hydrogen and $R^8$ is absent. The fraction of monomeric units which include the aminoalkyl or ammonioalkyl group can be from about 5% to about 90% of the monomeric units of the polymer.

The spacer group is a component of the polymer side chain and connects the amino or ammonium group to the polymer backbone. The amino or ammonium group is, thus, a pendant group. The spacer group can be a normal or branched, saturated or unsaturated, substituted or unsubstituted alkylene group, such as a polymethylene group —$(CH_2)_n$—, wherein n is an integer from about 2 to about 15. Suitable examples include the propylene, hexylene and octylene groups. The alkylene group can also, optionally, be interrupted at one or more points by a heteroatom, such as an oxygen, nitrogen (e.g, NH) or sulfur atom. Examples include the oxaalkylene groups —$(CH_2)_2O[(CH_2)_2O]_n(CH_2)_2$—, wherein n is an integer ranging from 0 to about 3.

Polymers to be administered which have quaternary ammonium groups or protonated amino groups will further comprise a pharmaceutically acceptable counter anion, such as anions which are conjugate bases of the pharmaceutically acceptable acids discussed above, for example, chloride, bromide, acetate, formate, citrate, ascorbate, sulfate or phosphate. The number of counter anions associated with the polymer prior to administration is the number necessary to balance the electrical charge on the polymer.

The polymer can also be a copolymer further comprising a hydrophobic monomer. The hydrophobic monomer can comprise a side chain bearing a hydrophobic group, such as a straight chain or branched, substituted or unsubstituted $C_3$–$C_{18}$-alkyl group or a substituted or unsubstituted aryl group. Examples of suitable hydrophobic monomers include styrene, N-isopropylacrylamide, N-t-butylacrylamide, N-n-butylacrylamide, heptafluorobutylacrylate, N-n-decylallylamine, N-n-decylacrylamide, pentafluorostyrene, n-butylacrylate, t-butylacrylate, n-decylacrylate, N-t-butylmethacrylamide, n-decylmethacrylate, and n-butylmethacrylate.

Examples of copolymers comprising a monomer of Formula I and a hydrophobic monomer include poly(N-(3-dimethylaminopropyl)acrylamide-co-N-(n-butyl) acrylamide) or salts thereof with pharmaceutically acceptable acids. Other examples of suitable copolymers include poly(2-trimethylammoniumethylmethacrylate-co-styrene) chloride, poly(2-trimethylammoniumethylmethacrylate-co-N-isopropylacrylamide) chloride, poly(2-trimethylammoniumethylmethacrylate-co-heptafluorobutylacryl) chloride, poly(3-trimethylammoniumpropylmethacrylate-co-styrene) chloride, poly(3-trimethylammoniumpropylmethacrylate-co-N-t-butylacrylamide) chloride, poly(3-trimethylammoniumpropylmethacrylate-co-N-n-butylacrylamide) chloride, and poly(N-(3-trimethylammoniumpropyl)allylamine-co-N-n-decylallylamine). Each of these ionic copolymers can also be employed with counter ions other than chloride, for example, a conjugate base of a pharmaceutically acceptable acid.

In a further embodiment, the polymer to be administered comprises a monomer of Formula I, a hydrophobic monomer and a neutral hydrophilic monomer, such as acrylamide, methacrylamide, N-(2-hydroxyethyl)acrylamide or 2-hydroxyethylmethacrylate. Examples of polymers of this type include terpolymers of N-(3-trimethylammoniumpropyl)methacrylamide/N-isopropylacrylamide/2-hydroxyethyl-methacrylate, N-(3-trimethylammoniumpropyl)methacrylamide/N-n-decylacrylamide/2-hydroxyethylmethacrylate, N-(3-trimethylammoniumpropyl)methacrylamide/N-t-butylmethacrylamide/methacrylamide, N-(3-trimethylammoniumpropyl) methacrylamide/n-decylacrylate/methacrylamide, 2-trimethylammoniumethylmeth-acrylate/n-butyl-acrylate/acrylamide, 2-trimethylammonium-ethylmethacrylate/t-butylacrylate/acrylamide, 2-trimethylammoniumethylmethacrylate/n-decylacrylate/acrylamide, 2-trimethylammonium-ethylmethacrylate/n-decylmethacrylate/methacrylamide, 2-trimethylammoniumethylmethacrylate/N-t-butyl-methacrylamide/methacrylamide and 2-trimethylammoniumethylmethacrylate/N-n-butyl-methacrylamide/methacrylamide.

The polymer to be administered can be an addition polymer having a polymer backbone such as a polyacrylate, polyacrylamide, poly(allylalcohol), poly(vinylalcohol), poly (vinylamine), poly(allylamine), or polyalkyleneimine backbone. The polymer can have a uniform backbone if it is composed of monomers derived from a common polymerizable unit, such as acrylamide. If the polymer is a copolymer, it can also comprise a mixed backbone, for example, the monomer of Formula I can be an acrylamide derivative, while the hydrophobic monomer can be a styrene derivative. The polymers disclosed herein include examples of both uniform and mixed backbones.

The polymers of use in the present method also include condensation polymers, wherein polymerization of monomers is accompanied by the release of a small molecule, such as a water molecule. Such polymers include, for example, polyesters and polyurethanes.

The polymers of use in the present method are preferably substantially nonbiodegradable and nonabsorbable. That is, the polymers do not substantially break down under physiological conditions into fragments which are absorbable by body tissues. The polymers preferably have a nonhydrolyzable backbone, which is substantially inert under conditions encountered in the target region of the body, such as the gastrointestinal tract.

The composition of the copolymers to be administered can vary substantially. The copolymer can comprise from about 95 mole percent to about 5 mole percent, preferably from about 20 mole percent to about 80 mole percent, of a monomer of Formula I. The copolymer can also comprise from about 95 mole percent to about 5 mole percent, preferably from about 20 mole percent to about 80 mole percent, of a hydrophobic monomer.

The polymer to be administered will, preferably, be of a molecular weight which is suitable for the intended mode of administration and allows the polymer to reach and remain within the targeted region of the body for a period of time sufficient to interact with the infecting organism. For example, a method for treating an intestinal infection should utilize a polymer of sufficiently high molecular weight to resist absorption, partially or completely, from the gastrointestinal tract into other parts of the body. The polymers can have molecular weights ranging from about 500 Daltons to about 500,000 or to about 1 million Daltons, preferably from about 2,000 Daltons to about 150,000 Daltons, to about 500,000 or to about 1 million Daltons.

The polymers which are useful in the present method can be prepared by known methods. A first method includes the direct polymerization of a monomer, such as trimethylammoniummethylacrylate chloride, or a set of two or more monomers, such as trimethylammoniummethyl-acrylate chloride, N-n-butylacrylamide and acrylamide. This can be accomplished via standard methods of free radical, cationic or anionic polymerization which are well known in the art. Due to reactivity differences between two monomers, the composition of a copolymer produced in this way can differ from the composition of the starting mixture. This reactivity difference can also result in a nonrandom distribution of monomers along the polymer chain.

A second method proceeds via the intermediacy of an activated polymer comprising labile side chains which are readily substituted by a desired side chain. An example of a suitable activated polymer is the succinimide ester of polyacrylic acid, poly(N-acryloyloxysuccinimide) (also referred to hereinafter as "pNAS"), which reacts with nucleophiles such as a primary amine to form a N-substituted polyacrylamide. Another suitable activated polymer is poly(paranitrophenylacrylate), which react with amine nucleophiles in a similar fashion.

Polymers suitable for use in the present method can also be prepared by addition of a side chain to a preformed polymer. For example, poly(allylamine) can be alkylated at the amino nitrogen by one or more alkylating agents. For example, one fraction of amino groups can be alkylated using a normal or branched ($C_3$–$C_{18}$-alkyl halide, such as n-decyl bromide, while another fraction can be alkylate by a quaternary ammonium-containing alkyl halide, such as 1-trimethylammonium-4-bromombutane.

A copolymer having a polyacrylamide backbone comprising amide nitrogens bearing two different substituents can be prepared by treating p(NAS) with less than one equivalent (relative to N-acryloyloxysuccinimide monomer) of a first primary amine, producing a poly(N-substituted acrylamide-co-N-acryoyloxysuccinimide) copolymer. Remaining N-acryoyloxysuccinimide monomer can then be reacted with, for example, an excess of a second primary amine to produce a polyacrylamide copolymer having two different N-substituents. A variety of copolymer compositions can, thus, be obtained by treating the activated polymer with different proportions of two or more amines.

An additional aspect of the present invention is a method for treating a microbial infection in a mammal, such as a human, comprising administering to the mammal a synergistically effective combination therapy regimen comprising an antibacterial agent and a polymer having an amino group or an ammonium group within the polymer backbone. The polymer can have, for example, a polymethylene, backbone which is interrupted by one or more amino or ammonium groups. An example of a polymer of this type is poly(decamethylenedimethylammonium-co-ethylenedimethylammonium) bromide, which is synthesized via the reaction of N,N,N',N'-tetramethylethylenediamine and 1,10-dibromodecane. The polymer can also be administered in association with anions other than bromide, such as chloride or acetate anions. Other examples include poly(alkyleneimines), for example, poly(ethyleneimine). Such polymers can comprise secondary or tertiary amino groups, salts of such groups with pharmaceutically acceptable acids, and/or quaternary ammonium groups.

Examples of other such suitable polymer include polymers comprising piperidine or pyridine groups within the backbone of the polymer (e.g. 4, 4'-Trimethylenedipyridine-alt-1,5 dibromopentane and 4,4-trimethylenepiperidine-alt-a, 6 dibromohexane).

As discussed below in Examples 35–42, several polymers described herein were tested in combination with an antibiotic for in vitro activity against Cryptosporidium parvum infectivity in mammalian cell culture and in vivo activity in mice.

The invention will now be further and specifically described by the following examples.

EXAMPLES

The following abbreviations are used throughout the examples to denote the following monomers:

MAPTAC, N-(3-trimethylammoniopropyl) methacrylamide chloride;

TMAEMC, 2-trimethylammonioethylmethacrylate chloride;

HEMA, 2-hydroxyethylmethacrylate;

TMAEAC 2-trimethylammonioethylacrylate chloride.

The copolymers and terpolymers of the following examples are given nominal compositions which correspond to the molar ratios of starting monomers in the copolymerization mixture.

Example 1

Synthesis of poly(N-acryloyloxysuccinimide) (pNAS)

A solution of N-acryloyloxysuccinimide (25.0 g, 148 mmole) in 100 mL dry DMF was degassed by nitrogen purging and simultaneously heated to 60° C. To the reaction mixture was added azobisisobutyronitrile (AIBN) (120 mg, 0.005 equivalents with respect to monomer). The reaction was allowed to proceed for 24 hours at 60° C. The polymer solution was cooled to room temperature and poured into rapidly stirred THF. The resulting white precipitate was filtered, washed with THF and dried in vacuo.

Example 2

Synthesis of poly(N-(3-dimethylamino-propyl) acrylamide-co-N-n-butylacrylamide)

To a solution of 3.0 g (17.75 mmole) pNAS in 20 mL dry DMF was added 0.6 g (3.55 mmole) n-butylamine. The resulting solution was stirred at room temperature for 14 hours, and then heated at 60° C. for 4 hours. After the solution was cooled to room temperature, 9.05 g (89 mmole) 3-dimethylaminopropylamine was added, and the resulting solution was stirred at room temperature for 2 hours, then heated to 60° C. for 20 hours. After cooling to room temperature, the solution was diluted with 25 mL water, and dialyzed against water for 24 hours. The solution was then lyophilized to afford poly(N-(3-dimethylaminopropyl-acrylamide)-co-N-n-butylacrylamide) as a tacky white solid.

Example 3

Synthesis of poly(N-(3-trimethylammoniopropyl) acrylamide-co-N-n-butylacrylamide) iodide To a suspension of poly(3-dimethylaminopropyl-acrylamide-co-N-n-butylacrylamide in methanol was added 0.5 g methyl iodide. The resulting mixture was stirred for 3 hours, and gradually became homogeneous. After stirring for another 12 hours, the solvent was removed under reduced pressure and the polymer was washed with dry hexane.

Example 4

Synthesis of poly(N-(2-hydroxyethyl)acrylamide-co-N-(6-trimethylammoniohexyl)acrylamide) bromide To a solution of 2.48 g (15 mmole) pNAS in 5 mL DMF was added 1.00 g mmole) 1-trimethylammonium-6-hexanamine bromide. The solution was stirred at room temperature for 4 hours and then heated at 60° C. for 20 hours. The solution was cooled to room temperature, and then 8.95 g (150 mmole) 2-ethanolamine was added. The resulting mixture was heated to 80° C. for 20 hours, cooled to room temperature and diluted with 10 mL water. The solution was dialyzed against water for 24 hours, then lyophilized, yielding the polymer as a brittle white solid.

Example 5

Synthesis of poly(TMAEAC)

A solution of 48.25 g (0.25 mol) 2-trimethylammonioethylacrylate chloride in 400 mL isopropanol was degassed by nitrogen purging and heated to 35° C. To this stirred solution was added a solution of 0.8 g potassium persulfate in 10 mL distilled water. A slight exotherm was observed. The solution was stirred at 35° C. for 6 hours, then cooled to room temperature. The solution was added to hexanes and the resulting precipitate was isolated by filtration.

Example 6

Synthesis of poly(decamethylenedimethylammonium-co-ethylenedimethylammonium) bromide N,N,N',N'-tetramethylethylenediamine (10.0 g Aldrich), 1,10-dibromodecane (25.8 g, Aldrich) and methanol (100 mL) were placed into a three-neck 250 mL round bottom flask. The mixture was heated with gentle stirring to 65° C. for 6 days, at which point methanol (40 mL) was added, and the mixture was refluxed for an additional 2 days. The mixture was then dripped into acetone, forming a solid that was collected by filtration, rinsed with acetone, and dried in a vacuum oven to yield 30.9 g of product.

Example 7

Synthesis of poly(TMAEMC-co-styrene) 75/25

A 500 mL round bottomed flask was charged with trimethylammonioethylmethacrylate chloride (26.0 g of a 70 wt % aqueous solution, 18.2 g), styrene (6.0 g) and isopropanol (150 mL). The solution was degassed by the addition of a rapid stream of nitrogen for 10 minutes, followed by the addition of AIBN (0.5 g). The solution was degassed for a further thirty minutes and, while continuing the addition of nitrogen, the solution was heated to 70° C., and the temperature maintained for 17 hours. The polymer began to precipitate within 2 hours, and by the completion of the reaction a sticky white precipitate had formed. The reaction mixture was cooled, the isopropanol was decanted from the polymer, and the polymer was dissolved in methanol. Dropwise addition of the methanol solution to ethyl acetate (1200 mL) caused the polymer to precipitate as a fine white powder which was recovered by filtration.

Example 8

Synthesis of poly(TMAEMC-co-N-isopropylacrylamide) (67/33)

A 500 mL round bottomed flask was charged with trimethylammonioethylmethacrylate chloride (14.5 g of a 70 wt % aqueous solution, 10.0 g), N-isopropylacrylamide (5.0 g) and isopropanol (150 mL). The solution was degassed by the addition of a rapid stream of nitrogen for 10 minutes, followed by the addition of AIBN (0.5 g). The solution was degassed for a further 60 minutes. The reaction mixture was heated to 70° C., and the temperature maintained for 16 hours. The polymer partially precipitated over the course of the reaction. Upon cooling, the propanol was decanted from the polymer, and the polymer was dissolved in methanol. Precipitation of the methanol solution dropwise into ethyl acetate (1200 mL) caused the polymer to be deposited as white curds which were recovered by filtration, washed with ethyl acetate, and dried in vacuo.

Additional TMAEMC/N-isopropylacrylamide copolymers were prepared by a similar method with the starting monomers in the following ratios: TMAEMC/N-isopropylacrylamide=40/60, 25/75 and 15/85.

Example 9

Synthesis of poly(MAPTAC-co-styrene) 75/25

To isopropanol (150 mL) was added a solution of N-(3-trimethylammonio-propyl)methacrylamide chloride in water (50 wt % solution, 24.0 g, 12.0 g of monomer). To this solution was added styrene (6.0 g), followed by the addition of AIBN (0.5 g). The homogeneous solution was degassed by bubbling a stream of nitrogen through it for 30 minutes. The solution was heated to 70° C. for 15 hours. The polymer partially precipitated as the reaction proceeded. The solution was cooled, the isopropanol was decanted off, the white solid was washed with propanol (50 mL). The propanol was decanted a second time, and the solid was dissolved in methanol (150 mL). The clear solution was added dropwise to ethyl acetate, causing the polymer to be precipitated as a white powder. The polymer was recovered by filtration, washed with 50 mL of ethylacetate and air dried.

An additional MAPTAC/styrene copolymer was prepared by a similar method employing a 50/50 mixture of starting monomers.

Example 10

Synthesis of poly(TMAEMC-co-heptafluorobutylacrylate) 75/25

A 500 mL round bottomed flask was charged with 2-trimethylammonioethylmethacrylate chloride (26.0 g of a 70 wt % aqueous solution, 18.2 g), heptafluorobutylacrylate (6.0 g) and isopropanol (150 mL). The solution was degassed by the addition of a rapid stream of nitrogen for 10 minutes, followed by the addition of AIBN (0.5 g). The solution was degassed for a further thirty minutes and, continuing the addition of nitrogen, the solution was heated to 70° C. The temperature was maintained for 17 hours. The polymer began to precipitate within 1 hour, and by the completion of the reaction a sticky white precipitate had formed. The reaction mixture was cooled, the propanol was decanted from the polymer, and the polymer was dissolved in methanol (100 mL). Precipitation of the methanol solution dropwise into ethyl acetate (1200 mL) caused the polymer to be deposited as a white solid which was recovered by filtration.

Example 11

Synthesis of poly(MAPTAC-co-N-t-butylacrylamide) 75/25

To a 500 mL round-bottom, three-neck flask fitted with a thermocouple, reflux condenser, and septum was added 36.4 g of a 50% aqueous solution of N-(3-trimethylammoniumpropyl)methacrylamide chloride and 6 g of N-t-butylacrylamide followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting reaction mixture consisted of two phases. The turbid liquid phase was decanted from the bulk of the reaction which was a white sticky solid phase. The liquid was precipitated into 1200 mL of ethyl acetate and filtered by vacuum filtration through a Buchner funnel. The white hygroscopic precipitate was dried in vacuo. The solid phase was dissolved in methanol and precipitated into 1200 mL of ethyl acetate and filtered by vacuum filtration to yield a white powder which was stored under vacuum.

Additional MAPTAC/N-t-butylacrylamide copolymers were prepared by a similar method beginning with the starting monomers in the following ratios: N-(3-trimethylammoniopropyl)methacrylamide/N-t-butylacrylamide =60/40, 50/50, 40/60, and 25/75.

Example 12

Synthesis of poly(N-decylallylamine-co-N-(4-timethylammoniobutyl) allylamine)

To a solution of poly(allylamine) HCl (20.15 g of a 50 wt % aqueous solution) was added sodium hydroxide (5.64 g) as a solid. The solution was stirred for 40 minutes, filtered and the filter cake was washed with methanol (15 mL). The solution was further diluted with methanol (25 mL) and to the solution was added 1-bromodecane (7.73 g, 35 mmol) and (1-trimethylamino-4-bromobutane) chloride (9.13 g, 35 mmol). A solution was prepared of sodium hydroxide (2.8 g, 70 mmol) in water (5 mL). This solution was added to the reaction mixture in four portions at thirty minute intervals. The solution was then stirred at room temperature for 24 hours, followed by dialysis against deionized water and freeze-dried. A total of 23.2 g of a glassy, hygroscopic solid was recovered.

Example 13

Synthesis of poly(TMAEMC-co-N-t-butylacrylamide) 57/43

To a 500 ml, round-bottom, three-neck flask fitted with a thermocouple, reflux condenser, and septum was added 18.20 g of a 70% aqueous solution of 2-trimethylammonium-ethylmethacrylic chloride and 9.7 g of N-t-butylacrylamide followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting reaction mixture consisted of two easily separable phases. The liquid phase was decanted from the bulk of the reaction which was a white solid. The liquid was precipitated into 1200 mL of ethyl acetate and filtered by vacuum filtration through a Buchner funnel. The white precipitate was dried in vacuo and weighed: fraction A, 10.1 g (45.1% yield based on 22.4 g monomers added). The solid phase was dissolved in methanol and precipitated into 600 mL of ethyl acetate and filtered by vacuum filtration to yield fraction B, 5.81 g of a white powder (25.9% yield) which was dried under vacuum.

TMAEMC/N-t-Butylacrylamide copolymers were also prepared by a similar method with the starting monomers in the following ratios: TMAEMC/N-t-Butylacrylamide=63/37, 50/50, 40/60, 25/75, 15/85 and 5/95.

Example 14

Synthesis of poly(MAPTAC-co-N-n-decylacrylamide) 75/25

To a 500 mL round-bottom, three-neck flask fitted with a thermocouple, reflux condenser, and septum was added 36.4 g of a 50% aqueous solution of N-(3-trimethylammoniopropyl)methacrylamide chloride and 6 g of N-n-decylacrylamide followed by 150 mL of isopropanol. The solution was purged with nitrogen for 1 hour and 0.5 g AIBN was added. The mixture was purged for 15 minutes until all of the AIBN dissolved. The solution was heated to 75° C. under nitrogen for 16 hours.

The reaction mixture consisted of two easily separable phases. The clear, yellow liquid phase was precipitated into 1200 mL of ethyl acetate. The precipitate was isolated by filtration and dried under vacuum to yield 2.14 g of a yellow powder, fraction A (8.84% yield). Methanol was added to the creamy yellow reaction precipitate and the resulting turbid yellow solution was precipitated into 1200 mL of ethyl acetate. The white precipitate was isolated by filtration and dried under vacuum to yield fraction B, 17.22 g, as a slightly yellow powder (71.2% yield).

Additional MAPTAC/N-n-decylacrylamide copolymers were prepared by a similar method with the starting monomers in the following ratios: MAPTAC/N-n-decylacrylamide=60/40, 50/50, and 40/60.

Example 15

Synthesis of poly(TMAEMC-co-pentafluorostyrene) 75/25

To a 500 mL round-bottom, three-neck flask fitted with a thermocouple, reflux condenser, and septum was added 26.0 g of a 70% aqueous solution of 2-trimethylammonium-ethylmethacrylate chloride and 6 g of pentafluorostyrene followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of two phases. The turbid solution was discarded. The bulk of the reaction, consisting of a white solid mass at the bottom of the flask, was dissolved in methanol. The resulting clear solution was precipitated into 1200 mL of ethyl acetate. The white precipitate was isolated by vacuum filtration to yield 20.39 g of a fine white powder (84.3% yield).

Additional TMABMC/pentafluorostyrene copolymers were prepared by a similar method with the starting monomers in the following ratios: TMAEMC/pentafluorostyrene=60/40 and 50150.

Example 16

Synthesis of poly(MAPTAC-co-pentafluorostyrene) 75/25

To a 500 mL round-bottom, three-neck flask fitted with a thermocouple, reflux condenser, and septum was added 36.3 g of a 50% aqueous solution of N-(3-trimethylammoniopropyl)methacrylamide chloride and 6 g of pentafluorostyrene followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a turbid solution with a white precipitate. The supernatant was discarded. The white reaction precipitate was dissolved in methanol and the resulting clear solution was precipitated into 1200 mL of ethyl acetate. The white precipitate was isolated by filtration and dried under vacuum to yield 12.81 g of a fine white powder (52.9% yield).

Additional MAPTAC/pentafluorostyrene copolymers were prepared by a similar method with the starting monomers in the following ratios: MAPTAC/pentafluorostyrene= 60/40 and 50/50.

Example 17

Synthesis of MAPTAC/N-t-Butylacrylamide/HEMA Terpolymer 33/33/33

To a 500 mL round-bottom, three-neck flask fitted with a thermocouple, reflux condenser, and septum was added 150 mL of isopropanol followed by 16.1 g of a 50% aqueous solution of N-(3-trimethylammoniopropyl)methacrylamide chloride, 8 g of N-t-butylacrylamide, and 8 g of 2-hydroxyethylmethacrylate. The solution was purged with nitrogen for 1 hour and 0.5 g of AIBN was added. The mixture was purged for ~15 minutes until all of the AIBN dissolved. The solution was heated to 75° C. under nitrogen for 16 hours.

The reaction mixture consisted of a turbid solution with a white latex in the bottom of the flask. The solution was precipitated into 1200 mL of ethyl acetate. The white precipitate was isolated by filtration to yield a sticky white powder which was dried under vacuum to yield 10.43 g of a lumpy white solid (fraction A) (43.1% yield). The white reaction precipitate was dissolved in methanol and precipitated into 1200 mL of ethyl acetate. The precipitate was isolated by filtration and dried under vacuum to yield 8.89 g of a fine white powder (fraction B) (36.7% yield).

Additional MAPTAC/N-t-butylacrylamide/HEMA terpolymers were prepared by a similar method beginning with the following ratios of the starting monomers: MAPTAC/N-t-Butylacrylamide/HEMA=28/43/28, 23/53/23, and 18/63/18.

Example 18

Synthesis of MAPTAC/N-Isopropylacrylamide/ HEMA Terpolymer 18/63/18

To a 500 mL round-bottom, three-neck flask fitted with a thermocouple, reflux condenser, and septum was added 150 mL of isopropanol followed by 8.9 g of a 50% aqueous solution of N-(3-trimethylammoniopropyl)methacrylamide chloride, 15.3 g of N-iso-propylacrylamide, and 4.4 g of 2-hydroxyethylmethacrylate. The solution was purged with nitrogen for 1 hour and 0.5 g of AIBN was added. The mixture was purged for 15 minutes until all of the AIBN dissolved. The solution was heated to 75° C. under nitrogen for 16 hours.

The clear slightly pink reaction solution was precipitated into 1200 mL of ethyl acetate. The precipitate was isolated by filtration to yield a sticky white solid which was dried under vacuum to yield 14.42 g of a hard clear/white granular solid (59.6% yield).

Example 19

Synthesis of MAPTAC/N-Decylacrylamide/HEMA Terpolymer 33/33/33

To a 500 mL round-bottom, three-neck flask fitted with a thermocouple, reflux condenser, and septum was added 150 mL of isopropanol followed by 16.1 g of a 50% aqueous solution of N-(3-trimethylammoniopropyl)methacrylamide chloride, 8 g of N-decylacrylamide, and 8 g of 2-hydroxyethylmethacrylate. The solution was purged with nitrogen for 1 hour and 0.5 g of AIBN was added. The mixture was purged for ~15 minutes until all of the AIBN dissolved. The solution was heated to 75° C. under nitrogen for 16 hours.

The reaction mixture consisted of two phases. The clear yellow solution was precipitated into 1200 mL of ethyl acetate. The precipitate was isolated by filtration. The sticky yellow precipitate was dried under vacuum and the resulting brittle clear yellow foam was crushed to yield 4.98 g of a fine yellow granular powder (fraction A) (20.6% yield). The white reaction latex was dissolved in methanol and precipitated into 1200 mL of ethyl acetate. The precipitate was isolated by filtration and dried under vacuum to yield 10.24 g of a slightly yellow granular solid (fraction B) (42.3% yield).

Additional MAPTAC/N-Decylacrylamide/HEMA terpolymers were prepared by a similar method beginning with the following ratios of starting monomers: MAPTAC/N-Decylacrylamide/HEMA=28/43/28, 23/53/23, and 18/63/18.

Example 20

Synthesis of TMAEAC/n-Butylacrylate/Acrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of 2-trimethylammonioethylacrylate chloride, 7.26 g of n-butylacrylate, and 14.52 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting white reaction mixture was filtered by vacuum filtration through a Buchner funnel to yield a white powder. The powder was washed with isopropanol and dried under vacuum to yield 21.57 g of a fine white powder (89.1% yield based on 24.2 g of monomers).

Additional TMAEAC/n-butylacrylate/acrylamide terpolymers were prepared by a similar method beginning with the following ratios of starting monomers: TMAEMC/n-butylacrylate/acrylamide=20/20/60 and 30/10/60.

Example 21

Synthesis of TMAEAC/t-Butylacrylate/Acrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of 2-trimethylammonioethylacrylate chloride, 7.26 g of t-butylacrylate, and 14.52 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting white reaction mixture was filtered by vacuum filtration through a Buchner funnel to yield a white powder. The powder was washed with isopropanol and dried under vacuum to yield 21.13 g of a white powder (87.3% yield).

Additional TMAEAC/t-butylacrylate/acrylamide terpolymers were prepared by a similar method beginning with the following ratios of starting monomers: TMAEAC/t-butylacrylate/acrylamide=20/20/60 and 30/10/60.

Example 22

Synthesis of TMAEAC/n-Decylacrylate/Acrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of 2-trimethylammonioethylacrylate chloride, 7.26 g of n-decylacrylate, and 14.52 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting white reaction mixture was filtered by vacuum filtration through a Buchner funnel to yield a white powder. The powder was washed with isopropanol and dried under vacuum to yield 21.52 g of a fine white powder (89% yield).

Additional TMAEAC/n-decylacrylate /acrylamide terpolymers were prepared by a similar method beginning with the following ratios of starting monomers: TMAEAC/n-decylacrylate/acrylamide=20/20/60, and 30/10/60.

Example 23

Synthesis of MAPTAC/N-t-Butylmethacrylamide/Methacrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of N-(3-trimethylammoniopropyl)methacrylamide chloride, 7.26 g of N-t-butylmethacrylamide, and 14.52 g of methacrylamide. The solution was purged with nitrogen for 1 hour and 0.5 g of AIBN was added. The mixture was purged for ~15 minutes until all of the AIBN dissolved. The solution was heated to 75° C. under nitrogen for 16 hours.

The white reaction mixture was too difficult to filter by vacuum filtration so centrifugation techniques were employed instead. The reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 14.99 g of a slightly buff powder (61.9% yield).

Additional MAPTAC/N-t-butylmethacrylamide/ methacrylamide terpolymers were prepared by a similar method beginning with the following ratios of starting monomers: MAPTAC/N-tbutylmethacrylamide/methacrylamide=20/20/60, 33/33/33 and 30/10/60.

Example 24

Synthesis of MAPTAC/n-Decylmethacrylate/Methacrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of N-(3-trimethylammoniopropyl)methacrylamide chloride, 7.26 g of n-decylmethacrylate, and 14.52 of methacrylamide. The solution was purged with nitrogen for 1 hour and 0.5 g of AIBN was added. The mixture was purged for ~15 minutes until all of the AIBN dissolved. The solution was heated to 75° C. under nitrogen for 16 hours.

The isopropanol was decanted leaving a white chunky powder. Isopropanol was added and the mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 18.50 g of a granular white solid (76.4% yield).

Additional MAPTAC/N-decylmethacrylamide/ methacrylamide terpolymers were prepared by a similar method beginning with the following ratios of starting monomers: MAPTAC/N-decylmethacrylamide/methacrylamide=20/20/60, 33/33/33 and 30/10/60.

Example 25

Synthesis of TMAEMC/n-Decylmethacrylate/Methacrylamide Terpolymer 10/30/60

To a 500 mL round-bottom, three-neck flask fitted with a thermocouple, reflux condenser, and septum was added 150 mL of isopropanol followed by 3.46 g of a 70% aqueous solution of 2-trimethylammonioethylmethacrylate chloride, 7.26 g of n-decylmethacrylate, and 14.52 g of methacrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 10.29 g of a hard white solid (42.5% yield).

Additional TMAEMC/N-n-decylmethacrylamide/ methacrylamide terpolymers were prepared by a similar method beginning with the following ratios of starting monomers: TMAEMC/N-n-decylmethacrylamide/methacrylamide=20/20/60, 33/33/33 and 30/10/60.

Example 26

Synthesis of TMAEMC/N-t-Butylmethacrylamide/Methacrylamide Terpolymer 10/30/60

To a 500 mL, round-bottom, three-neck flask fitted with a thermocouple, reflux condenser, and septum was added 150 ml, of isopropanol followed by 3.46 g of a 70% aqueous solution of 2-trimethylammonioethylmethacrylate chloride, 7.26 g of N-t-butylmethacrylamide, and 14.52 g of methacrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 18.35 g of a fine white powder (75.8% yield).

Additional TMAEMC/N-t-butylmethacrylamide/ methacrylamide terpolymers were prepared by a similar method beginning with the following ratios of starting monomers: TMAEMC/N-t-butylmethacrylamide/ methacrylamide=20/20/60, 33/33/33 and 30/10/60.

Example 27

Synthesis of TMAEMC/n-Butylmethacrylate/ Methacrylamide Terpolymer 10/30/60

To a 500 mL round-bottom, three-neck flask fitted with a thermocouple, reflux condenser, and septum was added 150 mL of isopropanol followed by 3.46 g of a 70% aqueous solution of 2-trimethylammonioethylmethacrylate chloride, 7.26 g of n-butylmethacrylate, and 14.52 g of methacrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 20.99 g of a clumpy white powder (86.7% yield).

Additional TMAEMC/N-n-butylmethacrylamide/ methacrylamide terpolymers were prepared by a similar method beginning with the following ratios of starting monomers: TMAEMC/N-n-butylmethacrylamide/ methacrylamide=20/20/60 and 30/10/60.

Example 28

Synthesis of MAPTAC/n-Butylmethacrylate/ Methacrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of N-(3-trimethylammoniopropyl)methacrylamide chloride, 7.26 g of n-butylmethacrylate, and 14.52 g of methacrylamide. The solution was purged with nitrogen for 1 hour and 0.5 g of AIBN was added. The mixture was purged for ~15 minutes until all of the AIBN dissolved. The solution was heated to 75° C. under nitrogen for 16 hours.

The white reaction mixture was filtered by vacuum filtration to yield a white powder. The powder was washed with isopropanol and dried under vacuum to yield 22.20 g of a white powder (91.7% yield).

Additional MAPTAC/n-butylmethacrylate/ methacrylamide terpolymers were prepared by a similar method beginning with the following ratios of starting monomers: MAPTAC/n-butylmethacrylate/methacrylamide 20/20/60 and 30/10/60.

Example 29

Synthesis of TMAEAC/n-Decylacrylamide/ Acrylamide Terpolymer33/33/33

To a 500 mL round-bottom, three-neck flask fitted with a thermocouple, reflux condenser, and septum was added 150 mL of isopropanol followed by 16.13 g of a 50% aqueous solution of 2-trimethylammonioethylacrylate chloride, 8.06 g of n-decylacrylamide, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture was precipitated into 1200 mL of ethyl acetate. The fine precipitate was filtered by vacuum filtration to yield a sticky yellow material. The light yellow solid was dissolved in methanol and precipitated into 1200 mL of ethyl acetate. The precipitate was filtered by vacuum filtration to yield 10.85 g of a sticky, slightly yellow powder (44.8% yield).

Example 30

Synthesis of TMAEAC/N-t-Butylacrylamide/ Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammonioethylacrylate chloride, 8.06 g of N-t-butylacrylamide, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a clear colorless solution with a small amount of white sticky solid. The clear solution was precipitated into 1200 mL of ethyl acetate. The white precipitate was filtered, dissolved in water, and lyophilized to yield 6.65 of a white powder (27.5% yield).

Example 31

Synthesis of TNIAEAC/Styrene/Acrylamide Terpolymer 33/33/33

To a 500 mL round-bottom, three-neck flask fitted with a thermocouple, reflux condenser, and septum was added 150 ml, of isopropanol followed by 16.13 g of a 50% aqueous solution of 2-trimethylammonioethylacrylate chloride, 8.06 g of styrene, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a clear colorless solution and a white solid. The clear solution was discarded. The solid was dissolved in methanol, and precipitated into ethyl acetate (1200 mL). A white precipitate formed which settled out of the solution as a sticky white solid. The ethyl acetate was decanted and the solid dried by passing nitrogen through the flask. The solid was dissolved in water and lyophilized to yield 18.14 g of a fine white powder (75% yield).

Example 32

Synthesis of TMAEAC/n-Butylacrylate/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammonioethylacrylate chloride, 8.06 g of n-butylacrylate, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a clear colorless solution and a white chunky solid. The solution phase was discarded and the white solid dissolved in water, filtered and lyophilized to yield 12.84 of a fine white powder (53.1% yield).

Example 33

Synthesis of TMAEAC/n-Decylacrylate/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammonioethylacrylate chloride, 8.06 g of n-decylacrylate, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was precipitated into 1200 mL of ethyl acetate. The turbid solution was decanted and the polymer was dried with nitrogen, dissolved in water, and lyophilized to yield 8.79 g of fine white powder (36.3% yield).

Example 34

Synthesis of TMAEAC/t-Butylacrylate/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammonioethylacrylate chloride, 8.06 g of t-butylacrylate, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was precipitated into 1200 mL of ethyl acetate. The turbid solution was decanted and the polymer was dried with nitrogen, dissolved in water, and lyophilized to yield 6.51 g of fine white powder (26.9% yield).

Example 35

Synthesis of TMAEMC/n-hexyl methacrylate (75/25)

2-Trimethylammonium ethyl methacrylic chloride (75 mol %, 1.875 mol, 389.49 g, 556.42 g 70% aqueous solution) and n-hexyl methacrylate (25 mol %, 0.625 mol, 106.425 g) were dissolved in ethanol (3750 ml). The clear, pale yellow solution was degassed for 1.25 hour. AIBN (3 mol %, 75 mmol, 12.3 g) was added and the solution was degassed for an additional 45 minutes. The polymerization was run at 70° C. for 16 hours.

The polymer solution was precipitated into ethyl acetate (1:2). The polymer was redissolved in methanol (3500 ml) and reprecipitated into ethyl acetate (1:2). The sticky white polymer was washed with ethyl acetate (3000 ml). The polymer became brittle and was left overnight to dry in ethyl acetate (2000 ml). The resulting white brittle solid/powder was filtered, crushed, and dried in vacuo (426.1 g).

Example 36

Synthesis of TMAEMC/n-hexyl methacrylate (60/40)

2-Trimethylammonium ethyl methacrylic chloride (60 mol %, 1.5 mol, 311.595 g, 445.14 g 70% aqueous solution) and n-hexyl methacrylate (40 mol %, 1 mol, 170.28 g) were dissolved in methanol (3750 ml). The clear, pale yellow solution was degassed for 1.25 hour. AIBN (3 mol %, 75 nimol, 12.3 g) was added and the solution was degassed for an additional 45 minutes. The polymerization was run at 65° C. for 16 hours.

The solution was precipitated into ethyl acetate (1:6). The polymer was redissolved in ethanol and reprecipitated into ethyl acetate (1:3). The polymer was washed twice with ethyl acetate (2000 ml total) to give a fine white precipitate. The precipitate was dried in vacuo to yield a white powder (284.66 g).

Example 37

Synthesis of TMAEMC/styrene (55/45)

2-Trimethylammonium ethyl methacrylic chloride (55 mol %, 1.375 mol, 285.63 g, 408.04 g 70% aqueous solution) and styrene (45 mol %, 1. 125 mol, 117.17 g, 128.9 ml) were dissolved in methanol (2500 ml). The clear, pale yellow solution was degassed for 1.25 hour. AIBN (2 mol %, 50 mmol, 8.2 g) was added and the solution was degassed for an additional 45 minutes. The polymerization was run at 65° C. for 16 hours. The solution was precipitated into ethyl acetate (1:6). The white polymer was washed twice with ethyl acetate (2000 ml total). The powder was redissolved in ethanol (1750 ml) and reprecipitated into ethyl acetate (1:3). The polymer was washed twice with ethyl acetate (2000 ml total) and filtered. The precipitate was dried in vacuo to yield a white powder (387.51 g).

Example 38

Reaction of Poly(vinylamine) with 10 mol % n-hexyl bromide

Poly(vinylamine) (3.48 mol, 150 g, 461.53 g 32.5% aqueous solution, Mw 23K) was dissolved in ethanol (900 ml) followed by the addition of n-hexyl bromide (10 mol %, 0.348 mol, 49 ml). The resulting clear yellow solution was heated to 70° C., and sodium hydroxide (32 g of a 50 wt % solution) was added in 4 equal portions at 1 hour intervals. Heating was continued for 16 hours.

The clear orange reaction solution was precipitated into isopropanol acidified with 10% hydrochloric acid (4000 ml isopropanol/400 ml hydrochloric acid). The orange polymer was washed with isopropanol (1500 ml) and broken into small pieces. The polymer was redissolved in water (1250 ml) and poured into isopropanol (1:3). The resulting solution was milky with no precipitate.

More hydrochloric acid was added upon which fine white polymer precipitated. Hydrochloric acid was added until no further precipitate formed (122 ml). Isopropanol was added (2500 ml) to the precipitate/acidic isopropanol mixture and the mixture was allowed to stand overnight.

The precipitate was filtered and dried in vacuo (296.47 g).

Example 39

Reaction of Poly(ethyleneimine) with 20 mol % n-hexyl bromide

Poly(ethyleneimine) (8.12 mol, 350 g, 700 g 50% aqueous solution) was dissolved in ethanol (2100 ml) followed by n-hexyl bromide (1.62 mol, 268.2 g, 228.1 ml) to give a clear yellow solution. The solution was heated to 70° C., and sodium hydroxide (136 mL of a 50 wt % solution) was added in 4 equal portions at 1 hour intervals. Heating was continued for 16 hours.

The slightly turbid yellow solution was precipitated into isopropanol acidified with 10% hydrochloric acid (1:4). The sticky precipitate was allowed to sit in ethyl acetate overnight. The ethyl acetate was decanted and the sticky yellow polymer was dissolved in a minimum amount of water and reprecipitated into isopropanol (1:4). The precipitate was washed with ethanol and allowed to dry in vacuo. The resulting brittle polymer was crushed to yield a yellow powder (531.5 g).

Example 40

Reaction of Poly(ethyleneimine) with 10 mol % (4-bromobutyl)trimethylammonium bromide and 20 mol % 1-bromo-3-phenylpropane (4-bromobutyl)trimethylammonium bromide was prepared by the reaction of trimethylamine and 1,4-dibromobutane in methanol.

Poly(ethyleneimine) (8.12 mol, 350 g, 700 g of a 50% aqueous solution) was dissolved in ethanol (2100 ml) followed by (4-bromobutyl)trimethylammonium bromide (0.812 mol, 223.5 g) and 1-bromo-3-phenylpropane (1.63 mol, 247 ml). The slightly turbid yellow solution was heated to 70° C., and sodium hydroxide (208 g of a 50 wt % solution) was added in 4 equal portions at 1 hour intervals. The solution was heated for a total of 16 hours.

The turbid dark yellow reaction solution was precipitated into isopropanol acidified with 10% hydrochloric acid (1:3). The sticky yellow precipitate was washed twice with isopropanol (1000 ml), redissolved in water (2000 ml), and reprecipitated into isopropanol (1:3). The sticky polymer was washed several times with isopropanol and dried in vacuo. The resulting brittle yellow polymer was crushed to yield a yellow granular powder (802.9 g).

Example 41

Reaction of Poly(allylamine) with 10 mol % (4-bromobutyl)trimethylammonium bromide and 10 mol % n-hexyl bromide Poly(allylamine) hydrochloride (4.28 mol, 400 g, 800 g of a 50% aqueous solution) was dissolved in ethanol (850 ml) and heated to 75° C. Sodium hydroxide (66 mol %, 2.81 mol, 112.98 g, 225.98 g 50% aqueous solution) was added followed by water (500 ml) and (4-bromobutyl) trimethylammonium. bromide (0.428 mol, 117.63 g). Sodium hydroxide (0.428 mol, 17.12 g, 34.26 g 50% aqueous solution) was added in 4 equal portions over 4 hours. The reaction was allowed to proceed for a total of 16 hours.

Bromohexane (0.428 mol, 70.65 g) was added to the reaction mixture at 75° C. Sodium hydroxide (0.428 mol, 17.12 g, 34.26 g 50% aqueous solution) was added in 4 equal portions over 4 hours and the reaction was allowed to proceed for a total of 16 hours.

The reaction solution was precipitated into isopropanol acidified with 20% hydrochloric acid (5000 ml). The precipitate was washed twice with isopropanol (3000 ml) and filtered.

The polymer was redissolved in water (500 ml) and reprecipitated into isopropanol (4000 ml) precipitate was washed twice with isopropanol (4000 ml) and filtered. The polymer was dried in vacuo to yield a powder (600 g).

Example 42

Reaction of Poly(allylamine) with 10 mol % (3-chloropropyl) dimethyloctylammonium bromide (3-chloropropyl)dimethyloctylammonium bromide was prepared by the reaction of 1-bromo-3chloropropane and dimethyloctylamine in methanol.

Poly(allylamine) hydrochloride (4.28 mol, 400 g, 800 g of a 50% aqueous solution) was dissolved in ethanol (850 ml) and heated to 70° C. Sodium hydroxide (66 mol %, 2.81 mol, 112.98 g, 225.98 g 50% aqueous solution) was added followed by water (500 ml), (3-chloropropyl)dimethyl-octylammonium bromide (0.428 mol, 134.61 g), and water (300 ml). Sodium hydroxide (0.428 mol, 17.12 g, 34.26 g 50% aqueous solution) was added in 4 equal portions over 4 hours. The reaction was allowed to proceed for a total of 16 hours.

The reaction solution was precipitated into ethanol acidified with 20% hydrochloric acid (5000 ml). The precipitate was washed with isopropanol (3000 ml) and filtered.

The polymer was redissolved in water (1000 ml) and reprecipitated into isopropanol (4000 ml). The precipitate was washed with isopropanol (4000 ml) and filtered. The polymer was dried in vacuo to yield a powder (600 g).

Example 43

Reaction of Poly(allylamine) with 10 mol % (3-chloropropyl) dimethyloctylammonium bromide and 10 mol % benzyl bromide Poly(allylamine) hydrochloride (4.28 mol, 400 g, 800 g of a 50% aqueous solution) was dissolved in ethanol (850 ml) and heated to 70° C. Sodium hydroxide (66 mol %, 2.81 mol, 112.98 g, 225.98 g 50% aqueous solution) was added followed by water (500 ml), (3-chloropropyl)dimethyl-octylammonium bromide (0.428 mol, 134.61 g), and water (300 ml). Sodium hydroxide (0.428 mol, 17.12 g, 34.26 g 50% aqueous solution) was added in 4 equal portions over 4 hours. The reaction was allowed to proceed for a total of 17 hours.

Benzyl bromide (0.428 mol, 73.21 g, 50.91 ml) was added to the reaction mixture at 70° C. Sodium hydroxide (0.428 mol, 17.12 g, 34.26 g 50% aqueous solution) was added in 4 equal portions over 4 hours and the reaction was allowed to proceed for a total of 16 hours.

The reaction solution was precipitated into isopropanol acidified with 20% hydrochloric acid (5000 ml). The precipitate was washed with isopropanol and filtered.

The polymer was redissolved in water (500 ml) and reprecipitated into isopropanol (4000 ml). The precipitate was washed twice with isopropanol (4000 ml) and filtered. The polymer was dried in vacuo to yield a powder (600 g).

Example 44

Reaction of Poly(allylamine) with 10 mol % n-hexyl bromide

Poly(allylamine) hydrochloride (4.28 mol, 400 g, 800 g of a 50% aqueous solution) was dissolved in ethanol (850 ml) and heated to 75° C. Sodium hydroxide (66 mol %, 2.81 mol, 112.98 g, 225.98 g 50% aqueous solution) was added followed by water (500 ml) and n-hexyl bromide (0.428 mol, 70.65 g). Sodium hydroxide (0.428 mol, 17.12 g, 34.26 g 50% aqueous solution) was added in 4 equal portions over 4 hours. The reaction was allowed to proceed for a total of 16 hours.

The reaction solution was precipitated into isopropanol acidified with 20% hydrochloric acid (5000 ml). The precipitate was washed twice with isopropanol (3000 ml) and filtered.

The polymer was redissolved in water (500 ml) and reprecipitated into isopropanol (4000 ml). The precipitate was washed twice with isopropanol (4000 ml) and filtered. The polymer was dried in vacuo to yield a powder (600 g).

Example 45

Reaction of Poly(allylamine) with 10 mol % (bromomethyl)cyclohexane

Poly(allylamine) hydrochloride (4.28 mol, 400 g, 800 g 50% aqueous solution) was dissolved in ethanol (850 ml) and heated to 75° C. Sodium hydroxide (66 mol %, 2.81 mol, 112.98 g, 225.98 g 50% aqueous solution) was added followed by water (500 ml) and (bromomethyl)cyclohexane (0.428 mol, 75.79 g). Sodium hydroxide (0.428 mol, 17.12 g, 34.26 g 50% aqueous solution) was added in 4 equal portions over 4 hours. The reaction was allowed to proceed for a total of 16 hours.

The reaction solution was precipitated into isopropanol acidified with 20% hydrochloric acid (5000 ml). The precipitate was washed twice with isopropanol (3000 ml) and filtered.

The polymer was redissolved in water (500 ml) and reprecipitated into isopropanol (4000 ml). The precipitate was washed twice with isopropanol (4000 ml) and filtered. The polymer was dried in vacuo to yield a powder (500 g).

Example 46

Reaction of Poly(allylamine) with 10 mol % (3-bromopropyl)trimethylammonium bromide and 10 mol % benzyl bromide Poly(allylamine) hydrochloride (4.28 mol, 400 g, 800 g 50% aqueous solution) was dissolved in ethanol (850 ml) and heated to 75° C. Sodium hydroxide (66 mol %, 2.81 mol, 112.98 g, 225.98 g 50% aqueous solution) was added followed by water (500 ml) and (3-chloropropyl) dimethyloctylammonium bromide (0.428 mol, 111.63 g) and water (300 ml). Sodium hydroxide (0.428 mol, 17.12 g, 34.26 g 50% aqueous solution) was added in 4 equal portions over 4 hours. The reaction was allowed to proceed for a total of 16 hours.

Benzyl bromide (0.428 mol, 73.21 g, 50.91 ml) was added to the reaction mixture at 70° C. Sodium hydroxide (0.428 mol, 17.12 g, 34.26 g 50% aqueous solution) was added in 4 equal portions over 4 hours and the reaction was allowed to proceed for a total of 16 hours.

The reaction solution was precipitated into isopropanol acidified with 20% hydrochloric acid (5000 ml). The precipitate was washed with isopropanol and filtered.

The polymer was redissolved in water (600 ml) and reprecipitated into isopropanol (4000 ml). The precipitate was washed twice with isopropanol (4000 ml) and filtered. The polymer was dried in vacuo to yield a powder (500 g).

Example 47

Reaction of Poly(ethyleneimine) with 10 mol % 1-(3-chloropropyl)-pyridinium bromide 1-(3-chloropropyl)pyridinium bromide was prepared by the reaction of pyridine and 1-bromo-2-chloropropane. Pyridine (66 mL, 64.35 grams, 0.81 moles), 1,3-dibromopropane (166.23 grams, 0.82 moles) and tetrahydrofuran (150 mL) were added to a 1 L, round bottom flask equipped with air condensers and a magnetic stirring plate. The reagents were allowed to react at room temperature for 4 days. The reaction became cloudy as precipitate accumulated. Solids were collected by vacuum filtration, resuspended in tetrahydrofuran (250 mL) and collected by vacuum filtration. Solids were dried under vacuum at 35° C. for 24 hours. Yield 63.64 grams (0.27 moles, 30%).

Poly(ethyleneimine) (0.67 mol, 30 g, 60 g of a 50% aqueous solution) was diluted with water (160 ml). To this solution was added 1-(3-chloropropyl)pyridinium bromide (15.84 g, 67 mmol). The solution was heated to 65° C. Sodium hydroxide (67 mmol, 5.36 g of a 50 wt % solution) was added in four equal portions, spaced one hour apart. The solution was heated for a further 12 hours after the last addition of sodium hydroxide (for a total heating time of 16 hours). The slightly cloudy yellow solution was cooled and precipitated into a solution of 12M hydrochloric acid (75 ml) in isopropanol (1 L). The polymer was recovered by filtration, redissolved in water (300 mL) and precipitated into isopropanol. The polymer was recovered by filtration and dried at 40° C. in vacuo.

Example 48

Reaction of Poly(vinylamine) with 10 mol % 1-(3-chloropropyl)-pyridinium bromide Poly(vinylamine) (227 mmol, 10 g, 30 g of a 32.5 wt % aqueous solution) was diluted with water (150 ml). To this solution was added 1-(3-chloropropyl)pyridinium bromide (5.37 g, 22.7 mmol). The solution was heated to 75° C. Sodium hydroxide (22.7 mmol, 1.8 g of a 50 wt % solution) was added in three equal portions, spaced one hour apart. The solution was heated for a further 21 hours after the last addition of sodium hydroxide (for a total heating time of 24 hours). The clear solution was cooled and precipitated into a solution of 5% conc. hydrochloric acid in methanol (1200 ml). The very fine white polymer was recovered by filtration, washed with methanol, briefly air dried and dried in vacuo for 36 hours.

Example 49

Reaction of Poly(ethyleneimine) with 20 mol % decyl bromide and 10 mol % (4-bromobutyl) trimethylammonium bromide A solution was prepared of poly(ethyleneimine) (50 g of a 50 wt % aquous solution, 0.58 mol) in water (400 ml). To this solution was added (4-bromobutyl) trimethylammonium bromide (15.9 g, 58 mmol) in one portion. The solution was heated to 65° C., and to the clear yellow solution was added a solution of sodium hydroxide (4.64 g of a 50 wt % solution, 58 mmol) in three equal portions, spaced one hour apart. The solution was heated for a total of 12 hours, after which time decyl bromide (25.6 g, 116 mmol) was added in one portion. A further 9.28 g of a 50 wt % solution of sodium hydroxide was added in three portions, spaced one hour apart, and the solution was heated for a final period of 16 hours. The solution was cooled and precipitated in a solution of 5% conc. hydrochloric acid in methanol (2.5 L). The white polymer was filtered, washed with methanol (200 ml), redissolved in water (500 ml) and precipitated into isopropanol (1200 ml). The product was recovered by filtration, washed with propanol and dried in vacuo. Yield 86%.

Example 50

Reaction of Poly(ethyleneimine) with 20 mol % n-hexylbromide and 10 mol % (3-bromopropyl) trimethylammonium bromide A solution was prepared of poly(ethyleneimine) (50 g of a 50w % aqueous solution, 0.58 mol) in water (375 ml). To this solution was added (3-bromopropyl) trimethylammonium bromide(15.1 g, 5 8 mmol) in one portion. The solution was heated to 65° C., and to the clear yellow solution was added a solution of sodium hydroxide (4.64 g of a 50 wt % solution, 58 mmol) in three equal portions, spaced one hour apart. The solution was heated for a total of 10 hours, after which time n-hexyl bromide (19.14 g, 116 mmol) was added in one portion. A further 9.28 g of a 50 wt % solution of sodium hydroxide was added in three portions, spaced one hour apart, and the solution was heated for a final period of 14 hours. The solution was cooled and precipitated in a solution of 5% hydrochloric acid in methanol (2.3 L). The white polymer was filtered, washed with methanol (200 ml), redissolved in water (500 ml) and precipitated into isopropanol (1200 ml). The product was recovered by filtration, washed with propanol and dried in vacuo. Yield 81%.

Example 51

Reaction of Poly(allylamine) with 10 mol % 1-(3-chloropropyl) pyridinium bromide Poly(allylamine) hydrochloride (428 mmol, 40 g, 80 g 50% aqueous solution) was dissolved in water (200 ml) and heated to 70° C. Sodium hydroxide (66 mol %, 0281 mmol, 11.2 g, 22.4 g of 50% aqueous solution) was added. To this solution was added 1-(3-chloropropyl)pyridinium bromide (10.1 g, 42.8 mmol dissolved in 50 ml of water). Sodium hydroxide (42.8 mmol, 1.7 g, 3.4 g of 50% aqueous solution) was added in 3 equal portions over 4 hours. The reaction was allowed to proceed for a total of 16 hours. The reaction solution was precipitated into ethanol acidified with 10% hydrochloric acid (2000 ml). The precipitate was washed with isopropanol (300 ml) and filtered. The polymer was redissolved in water (200 ml), reprecipitated into isopropanol (800 ml) and dried in vacuo.

Example 52

Preparation of 3% Poly(allylamine/epichlorohydrin)

To a 4-L plastic beaker was added poly(allylamine) hydrochloride (2001.5 g of 50% aqueous solution; Nitto Boseki PAA-HCl-3L) and water (3L). The mixture was stirred until homogeneous and the pH was adjusted to ~10.5 with solid NaOH (280.3 g). The pH was reduced by adding concentrated hydrochloric acid until the pH was ~10.2. The solution was allowed to cool to room temperature in the beaker and epichlorohydrin (25 mL; 29.1 g, 3 mole %) was added all at once with stirring. The mixture was stirred gently until it gelled and then was allowed to continue curing for 18 hours at room temperature. The gel was then removed and broken up by passing it through a Kitchen Aid mixer. The solid was then suspended in ~16 L of deionized water. The gel was collected by filtration and washed on the funnel until the conductivity of the effluent was equal to 16.7 mS/cm. The solid was dried in a forced air oven at 60° C. for 5 days to yield 866.3 g of a granular, brittle, white solid. The solid was ground in a coffee grinder and passed through a 30 mesh sieve.

Example 53

Reaction of Poly(ethyleneimine) with 10 mol % benzyl bromide

Poly(ethyleneimine) (8.12 mol, 350 g, 700 g 50% aqueous solution) was dissolved in ethanol (2100 ml), followed by the addition of benzyl bromide (0.81 mol, 138.5 g). The solution was heated at 70° C. and to this solution was added sodium hydroxide (32.4 g, 64.8 g of a 50 wt % solution) in four portions spaced one hour apart. The solution was heated for a further 16 hours. The slightly turbid yellow solution was precipitated into isopropanol acidified with 10% hydrochloric acid (1:4) (5000 ml). The polymer was recovered by filtration, redissolved in water (1000 ml) and reprecipitated into propanol (3000 ml). The polymer was recovered by filtration and dried in vacuo.

Example 54

Reaction of Poly(allylamine) with 10 mol % n-decyl bromide and 10 mol % (10 bromodecyl) trimethylammonium bromide Poly(allylamine) hydrochloride (428 mmol, 40 g, 80 g of a 50% aqueous solution) was dissolved in water (200 ml) and heated to 70° C. Sodium hydroxide (66 mol %, 281 mmol, 11.2 g, 22.4 g of 50% aqueous solution) was added. To this solution was added (10-bromodecyl) trimethylammonium bromide (15.3 g, 42.8 mmol dissolved in 50 ml of water). Sodium hydroxide (42.8 mmol, 1.7 g, 3.4 g of 50% aqueous solution) was added in 3 equal portions over 4 hours. The reaction mixture was heated for a further 16 hours. Decyl bromide (9.45 g, 42.8 mmol) was added in one portion, followed by the addition of sodium hydroxide (42.8 mmol, 1.7 g, 3.4 g of 50% aqueous solution) which was added in 3 equal portions over 4 hours. The reaction was heated for a further 12 hours, cooled and precipitated into 1000 ml of ethanol containing 50 ml of conc. hydrochloric acid. The polymer was recovered by filtration and washed with ethanol (200 ml).

Example 55

Preparation of 4.5% cross-linked poly (diallylmethylamine)

83 g of an aqueous solution of poly(diallylmethylamine hydrochloride) (PAS-M-1, Lot No. 51017; Nitto Boseki Co.) was diluted with 170 mL deionized water. While stirring, 6.8 g NaOH was added to the polymer solution. The reaction mixture was allowed to stir until all NaOH had dissolved.

When the temperature of the solution had dropped to below 30° C., epichlorohydrin (1.2 mL) was added and stirring continued. The reaction medium slowly became viscous and after about 80 minutes, had gelled and the stirring was stopped. The polymer gel was left at room temperature for an additional 60 hours. The polymer slab was broken into smaller pieces and dispersed in 400 mL deionized water. The resulting suspension was stirred for 2 hours and then filtered. The swollen polymer particles were resuspended in 600 mL deionized water, stirred for 45 minutes and collected by filtration. The process was repeated with 800 mL water and 1 hour stirring. After filtration, the filtrate showed a conductivity of 4 mS/cm. The filtered polymer (swollen gel) was dried in a forced air oven at 60° C. to yield 42 g of product.

Example 56

Alkylation of Crosslinked Poly(diallylmethylamine) with 1-bromodecane 10 g of the ground polymer (Example 54) taken in a 1 liter 3-necked round bottom flask was suspended in 150 mL deionized water. The polymer swelled significantly and was stirred with a mechanical stirrer. While stirring, 2g 50% aqueous NaOH solution was added and the suspension was stirred for 15 minutes. To the suspension was then added 12.5 g 1-bromodecane dissolved in 32 mL ethanol and the reaction mixture was stirred for 2 hours. 1 g of 50% aqueous sodium hydroxide was then added and the reaction mixture was stirred at room temperature for 40 minutes followed by heating to 75° C. for 2 hours. 2 g NaOH solution was then added. The reaction mixture was stirred at 75° C. for an additional 18 hours, after which time heating was discontinued. After cooling to 30° C., 2 mL concentrated HCl was added and stirring was continued for 15 minutes. The polymer was filtered and washed with 200 mL deionized water, stirred with 200 mL water for fifteen minutes and filtered. This process was repeated twice and the filtered polymer was suspended in 400 mL 2M NaCl solution, stirred for 45 minutes and filtered. After removing the solvent by filtration, the polymer was suspended in 500 mL of 2 M NaCl solution and stirred for 40 minutes. The polymer was filtered and this process of NaCl treatment was repeated two more times. The filtered polymer was suspended in 400 mL deionized water. After stirring for 30 minutes the polymer was filtered and resuspended in 400 mL deionized water and stirred for 40 minutes. Concentrated HCl (1 mL) was added to the suspension and the mixture was stirred for 20 minutes. The pH of the suspension was found to be 2.25. After stirring for an additional 20 minutes, the polymer was filtered and dried at 60° C. in a forced air oven, yielding 16.8 g of the alkylated polymer. The polymer was ground and passed through a 140 mesh sieve.

Example 57

Reaction of 6%-cross-linked poly(allylamine) with 140 mol % 6-bromohexane and 170 mol % (6 bromohexyl)trimethylammonium bromide Methanol (5 L) and sodium hydroxide (133.7 g) were added to a 12 L round bottom flask equipped with a mechanical stirrer, a thermometer and a condenser. After the solid dissolved, 297 g 6% epichlorohydrin-crosslinked poly-allylamine was added along with additional methanol (3L). (6-Bromohexyl)trimethylammonium bromide (522.1 g) and 1-bromodecane (311.7 g) were added and the mixture was heated to 65° C. with stirring. After 18 hours at 65° C., the mixture was allowed to cool to room temperature. The solid was filtered off and rinsed by suspending, stirring for 30 minutes and filtering off the solid from 1.2×12 L methanol, 2.2×22 L aqueous NaCl (2 M), 3.3×22 L deionized water, 4.1×22 L isopropanol. The resulting solid was dried in a vacuum oven at 50° C. to yield 505.1 g of an off-white solid. The solid was then ground to pass through an 80 mesh sieve.

Example 58

Reaction of poly(allylamine) with 8 mole percent epichlorohydrin

To a 5 gallon bucket was added poly(allylamine) hydrochloride (2.5 kg) and water (10 L). The mixture was stirred until homogeneous and the pH was adjusted to 10 with solid NaOH. The solution was allowed to cool to room temperature in the bucket and epichlorohydrin (250 mL) was added all at once with stirring. The mixture was stirred gently until it gelled and then was allowed to continue curing for 18 hours at room temperature. The gel was then removed and put into a blender with isopropanol (about 7.5 L). The gel was mixed in the blender with about 500 mL isopropanol for about 3 minutes to form coarse particles and the solid was collected by filtration. The solid was rinsed three times by suspending it in 9 gallons of water, stirring the mixture for one hour and collecting the solid by filtration. The solid was rinsed once by suspending it in isopropanol (60 L) stirring the mixture for one hour and collecting the solid by filtration. The solid was dried in a vacuum oven for 18 hours to yield 1.55 kg of a granular brittle white solid.

Example 59

In vitro and in vivo activity of selected polymers in combination with paromomycin against C. Parvum infectivity.
TMAEMC/n-hexyl methacrylate (75/25) (Polymer A)
2-Trimethylammonium ethyl methacrylic chloride (75 mol %, 1.875 mol, 389.5 g, 556.4 g 70% aqueous solution) and n-hexyl methacrylate (25 mol %, 0.625 mol, 106.4 g) were dissolved in ethanol (3750 ml). The clear, pale yellow solution was degassed for 1.25 hours AIBN (3 mol %, 75 mmol, 12.3 g) was added and the solution was degassed for an additional 45 minutes. The polymerization was run at 70° C. for 16 hours.

The polymer solution was precipitated into ethyl acetate (1:2). The polymer was redissolved in methanol (3500 ml) and reprecipitated into ethyl acetate (1:2). The sticky white polymer was washed with ethyl acetate (3000 ml). The polymer became brittle and was left overnight to dry in ethyl acetate (2000 ml). The resulting white brittle solid/powder was filtered, crushed, and dried in vacuo (426.1 g).
Poly(allylamine) w/10% QC4Br, 10% n-hexyl bromide (Polymer B)
Poly(allylamine) hydrochloride (4.28 mol, 400 g, 800 g 50% aqueous solution) was dissolved in ethanol (850 ml) and heated to 75° C. Sodium hydroxide (66 mol %, 2.81 mol, 113 g, 226 g 50% aqueous solution) was added followed by water (500 ml) and QC4Br (0.428 mol, 117.63 g). Sodium hydroxide (0.428 mol, 17.12 g, 34.26 g 50% aqueous solution) was added in 4 equal portions over 4 hours. The reaction was allowed to proceed for a total of 16 hours.

Bromohexane (0.428 mol, 70.65 g) was added to the reaction mixture at 75° C. Sodium hydroxide (0.428 mol, 17.12 g, 34.26 g 50% aqueous solution) was added in 4 equal portions over 4 hours and the reaction was allowed to proceed for a total of 16 hours. The reaction solution was precipitated into isopropanol acidified with 20% hydrochloric acid (5000 ml). The precipitate was washed twice with isopropanol (3000 ml) and filtered.

The polymer was redissolved in water (500 ml) and reprecipitated into isopropanol (4000 ml). The precipitate was washed twice with isopropanol (4000 ml) and filtered. The polymer was dried in vacuo to yield a powder (600 g).

Poly(vinylamine) w/10% 3-chloropropyldimethylbutylammonium bromide (Polymer C)

Poly(vinylamine) (3.48 mol, 150 g, 461.53 g 32.5% aqueous solution, MW 23K) was dissolved in ethanol (900 ml) followed by the addition of 3-chloropropyldimethylbutylammonium bromide (10 mol %, 0.348 mol, 82.0 g). The clear yellow solution was heated at 70° C. A solution of sodium hydroxide (27.9 g of a 50 wt % solution) was added in three equal portions, spaced 1 hour apart. The solution was heated for a further 16 hours after the addition of the last aliquot of sodium hydroxide.

The clear yellow reaction solution was precipitated into isopropanol acidified with 10% hydrochloric acid (4000 ml isopropanol/400 ml hydrochloric acid). The off-white polymer was washed with isopropanol (1500 ml) and broken into small pieces.

The polymer was redissolved in water (1000 ml) and poured into isopropanol (4000 ml), causing the product to precipitate as a white fibrous material. The product was filtered, washed with 500 ml of propanol and dried in vacuo (260 g).

Poly(vinylamine) w/50% 3-chloropropyldimethylbutylammonium bromide (Polymer D)

Poly(vinylamine) (3.48 mol, 150 g, 461.53 g 32.5% aqueous solution, MW 23K) was dissolved in ethanol (900 ml) followed by the addition of 3-chloropropyldimethylbutylammonium bromide (10 mol %, 1.74 mol, 424 g).

The clear yellow solution was heated at 70° C. A solution of sodium hydroxide (139 g of a 50 wt % solution) was added in five equal portions, spaced 1 hour apart. The solution was heated for a further 14 hours after the addition of the last aliquot of sodium hydroxide.

The clear yellow reaction solution was precipitated into isopropanol acidified with 10% hydrochloric acid (5000 ml isopropanol/500 ml hydrochloric acid). The off-white polymer was washed with isopropanol (1500 ml) and broken into small pieces.

The polymer was redissolved in water (1500 ml) and poured into isopropanol (6000 ml), causing the product to precipitate as a white fibrous material. The product was filtered, washed with 500 ml of propanol and dried in vacuo (620 g).

Poly(allylamine) cross-linked w/1% ethylene glycol, diglycidyl ether w/30% QC4Br, 30% n-hexyl bromide (Polymer E)

To a solution of poly(allylamine) hydrochloride (0.55 mol, 100 g, 200 g 50% aqueous solution) was added sodium hydroxide (28.8 g, of a 50 wt % solution), followed by the addition of ethanol (106 ml) and water (63 ml). The mixture was heated to 60° C. with vigorous stirring. Heating was continued for 10 minutes, the solution was cooled to 30° C., and ethylene glycol, diglycidyl ether (426 μl, 1 mol %) was added. The solution was heated to 60° C. with vigorous heating for 10 hours. Bromohexane (23 ml, 0.16 mol) and 4-bromobutyldimethylammonium bromide (45.0 g, 0.16 mol) were added, each in one portion to form a dark yellow homogeneous solution. Sodium hydroxide (26.2 g of a 50 wt % solution) was added in three portions, spaced 1 hour apart, and the solution was heated for a further 16 hours after the addition of the last aliquot of sodium hydroxide. The reaction solution was cooled and was precipitated into isopropanol acidified with 10% hydrochloric acid (3000 ml). The precipitate was washed twice with isopropanol (300 ml) and filtered. The polymer was redissolved in water (500 ml) and reprecipitated into isopropanol (3000 ml). The precipitate was washed twice with isopropanol (400 ml) and filtered. The polymer was dried in vacuo to yield a powder (205 g).

Activity of polyfensin compounds for *Cryptosporidium parvum* in vitro. Combination therapy of Polymer B with paromomycin Madin Darby Bovine Kidney cells were infected with *C. parvum* oocysts in the presence of media alone, paromomycin (2 and 0.25 mg/ml), Polymer B (0.01 or 0.001 mg/ml) or Polymer B (0.01 or 0.001 mg/ml) plus paromomycin at 0.25 mg/ml. After 4 hours of treatment, polymer was removed and replaced with media. After 46 hours of infection the monolayers were fixed, stained with fluorescent antibodies to cryptosporidium, and the numbers of infected cells were enumerated. Parasite numbers represent the means of 12 high powered fields, and numbers of parasites were normalized relative to treatment with media alone (arbitrarily set at 100). Treatment with paromomycin (prm) alone at 2 or 0.25 mg/ml gave parasite numbers of 15.3 and 61.5 respectively; treatment with polymer alone at 0.01 mg/ml or 0.001 mg/ml gave parasite numbers of 7.7 and 53.8 respectively; treatment with 0.01 or 0.001 mg/ml polymer plus prm at 0.25 mg/ml gave parasite numbers of 3.8 and 23.4. These data indicate that the combination of polymer plus antibiotic were more than additive.

In vitro Combination therapy of Polymer A with paromomycin.

Madin Darby Bovine kidney cells were infected with *C. parvum* oocysts in the presence of media alone, paromomycin (2 and 0.25 mg/ml), Polymer A (0.01 or 0.001 mg/ml) or Polymer A (0.0 1 or 0.00 1 mg/ml plus paromomycin at 0.25 mg/ml).

After 4 hours of treatment, polymer was removed and replaced with media. After 46 hours of infection the monolayers were fixed, stained with fluorescent antibodies to cryptosporidium, and the numbers of infected cells were enumerated.

Parasite numbers represent the means of 12 high powered fields, and numbers of parasites were normalized relative to treatment with media alone (arbitrarily set at 100). Treatment with parmomycin (prm) alone at 2 or 0.25 mg/ml gave parasite numbers of 15.4 and 73.0 respectively; treatment with polymer alone at 0.01 mg/ml or 0.001 mg/ml gave parasite numbers of 69.1 and 96.1 respectively; treatment with 0.01 or 0.001 mg/ml polymer plus prm at 0.25 mg/ml gave parasite numbers of 11.5 and 23.1. These data indicate that the combination of polymer plus antibiotic were more than additive.

In vivo activity of selected polymers in combination with parmomycin

Severe combined immunodeficient mice (SCID) were infected with *C. parvum* oocysts on day 0. On day 7, mice were treated with water or Polymers A, E and D by delivery in maple flavored drinking water at 2000 mg/kg/day. For each treatment, mice additionally received water or 500 mg/kg/day paromomycin (prm) by oral gavage. Oocyst shedding was quantitated in fecal smears by acid fast staining. Average numbers of oocysts shed were as follows: Treatment with water alone, 25; treatment with prm alone 12. Treatment with polymers alone gave modest changes in oocysts shedding and ranged from ~20% reduction in oocysts; to a ~20% increase in shedding, relative to treatment with water alone. Combination of polymers with prm gave reductions in oocysts in the range of 50–90% relative to treatment with prm alone.

While this invention has been particularly shown and described with references to preferred embodiments thereof, it will be understood by those skilled in the art that various changes in form and details may be made therein without departing from the scope of the invention encompassed by the appended claims.

What is claimed is:

1. A treatment method for treating a microbial infection in a mammal, comprising administering to the mammal a combination of a therapeutically effective amount of an cationic polymer and a therapeutically effective amount of an antibacterial agent.

2. The method of claim 1 wherein the polymer further comprises a hydrophobic group connected to the polymer backbone.

3. The method of claim 1 wherein the mammal is a human.

4. The method of claim 1 wherein the microbial infection is a bacterial infection, a protozoal infection, an ameobic infection, a fungal infection or a parasitic infection.

5. The method of claim 1 wherein the polymer has an amino group, an ammonium group, a pyridyl group, or a piperidine group within the polymer backbone.

6. The method of claim 1 wherein said polymer comprises an amine or ammonium functional groups attached to the polymer backbone through aliphatic spacer groups.

7. A pharmaceutical composition having antibacterial effect comprising a therapeutically effective amount of an cationic polymer and an antibacterial agent.

* * * * *